United States Patent [19]
Greco et al.

[11] Patent Number: 4,778,838
[45] Date of Patent: Oct. 18, 1988

[54] STABILIZER COMPOUNDS AND PROCESS FOR THEIR PREPARATION

[75] Inventors: Alberto Greco, Dresano; Carlo Busetto, San Donato Milanese, both of Italy

[73] Assignee: Enichem Sintesi S.p.A., Palermo, Italy

[21] Appl. No.: 45,066

[22] Filed: May 1, 1987

[30] Foreign Application Priority Data

May 2, 1987 [IT] Italy ................................ 20297 A/86

[51] Int. Cl.$^4$ ...................... C08K 5/34; C07D 211/46; C07F 7/02
[52] U.S. Cl. ..................................... 524/99; 524/102; 546/14
[58] Field of Search ..................... 546/14; 524/99, 102

[56] References Cited

U.S. PATENT DOCUMENTS

| 4,141,883 | 2/1979 | Soma et al. | 546/14 |
| 4,177,186 | 12/1979 | Rody et al. | 546/14 |
| 4,210,578 | 7/1980 | Rody et al. | 546/14 |
| 4,518,416 | 5/1985 | Forster et al. | 546/14 |

Primary Examiner—Kriellion Morgan
Attorney, Agent, or Firm—Hedman, Gibson, Costigan & Hoare

[57] ABSTRACT

Siliconic compounds, stabilizer for organic polymers, containing in their molecule the aromatic phosphite or phosphonite function and the sterically hindered aminic function, are obtained by making a 2,2,6,6-tetramethyl-piperidinyl-4-oxyalkylene-γ-alkyl-di(alkyloxy)silane, an aliphatic glycol, an aromatic phosphite, phosphonite or diphosphite and possibly an aliphatic mono-hydroxy alcohol interact with each other.

10 Claims, No Drawings

STABILIZER COMPOUNDS AND PROCESS FOR THEIR PREPARATION

The present invention relates to siliconic compounds, stabilizer for organic polymers, containing in their molecule the aromatic phosphite or phosphonite function, and the sterically hindered aminic function. The invention relates also to the process for the preparation of said siliconic stabilizer compounds, as well as to the polymeric stabilized compositions, which comprise an organic polymer and a stabilizer amount of at least one of the said siliconic stabilizer compounds.

It is known that the organic polymers, such as the polyolefins and the polidienes, undergo degradation over time, by exposure to the atmospheric agents, in particular under to the action of U.V. light.

This degradation causes a reduction in the physical properties of the polymers, such as, e.g., a decrease in the ultimate tensile strngth and in flexibility, which are accompanied by a change in melt index.

In order to counteract such a degradation, it is usual in the art to introduce into the organic polymers small amounts of such stabilizer compounds as benzotriazoles, benzophenones and nickel complexes. Also useful to that purpose are organic compounds containing a sterically hindered aminic group, such as, e.g., the compounds deriving from 2,2,6,6-tetramethylpiperidine, as disclosed in U.S. Pat. No. 3,640,928.

In U.S. patent application Nr. 733,526 filed on May 13, 1985, now U.S. Pat. No. 4684725 there are disclosed stabilizer compounds for organic polymers, containing a sterically hindered aminic function, and bearing in their molecule also a hydrolysable silicic function. These stabilizer compounds, in the stabilization of the organic polymers, are hydrolysed in correspondence of the silicic function, and the silanol groups so produced are able to interact with each other, or with a solid support, or with the organic polymer to be stabilized, yielding, in any case, complex structures which remain stably inside the organic polymer.

In U.S. patent application No. 791.410 filed on Oct. 25, 1985, now abandoned there are disclosed stabilizer compounds for organic polymers, which are obtained by reacting a mono-hydroxy or poly-hydroxy aliphatic alcohol with a compound containing the alkoxysilane function and the sterically hindered aminic function. The so-obtained stabilizer compounds show, besides a high heat stability, the characteristics deriving from an easy dispersability and compatibility with the organic polymers.

In the art the stabilizer effect is furthermore known which is performed by the aromatic phosphites and phosphonites on the organic polymers. In particular, these compounds, used in combination with sterically hindered phenolic antioxidants, efficaciously counteract the oxidative decomposition of the organic polymers, sometimes showing a synergistic effect. On the contrary, no particularly advantageous results were obtained in the stabilization of the organic polymers by means of a stabilizer system consisting of a sterically hindered amine and an aromatic phosphite or phosphonite.

A class was found now of siliconic stabilizer compounds, which contain, in the same molecule, the sterically hindered aminic function and the aromatic phosphite or phosphonite function, which show, in the stabilization of the organic polymers, in particular polyolefins and polydienes, an unexpectedly intense action, however higher than as foreseeable on the basis of their content of the two above-mentioned functions. These siliconic stabilizer compounds have generally the appearance of colourless compounds, endowed with good fluidity, which are free from smell, and have a very long shelf life. They are furthermore perfectly compatible with the organic polymers, and are practically not extractable from the same polymers.

In accordance with the above, the present invention relates to siliconic stabilizer compounds for organic polymers, containing in their molecule the sterically hindered aminic function and the aromatic phosphite or phosphonite function, which are obtained from:

(a) a 2,2,6,6-tetramethyl-piperidinyl-4-oxyalkylene-γ-alkyl-di-(oxyalkyl)-silane, to be represented by the following general formula:

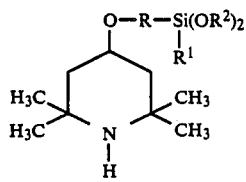

wherein:

R is an linear or branched alkylene group, containing from 1 to 6 carbon atoms, and preferably 3 carbon atoms:

$R^1$ and $R^2$, are equal to, or different from each other, and represent the methyl or ethyl group;

(b) an aliphatic di-hydroxy alcohol, to be represented by the general formula:

$$HO—R^3—OH$$

wherein $R^3$ is a linear or branched alkylene group, containing from 4 to 12 carbon atoms, and preferably 6 carbon atoms; or a cycloalkylene group;

(c) an aliphatic monohydroxy alcohol, to be represented by the general formula:

$$R^4—OH$$

wherein $R^4$ is a linear or branched alkyl group, containing from 1 to 10 carbon atoms, and preferably 4 carbon atoms;

(d) an aromatic phosphite, phosphonite or diphosphite selected from:

(i) phosphites or phosphonites definable by the general formula:

wherein $R^5$ and $R^6$ are the phenyl group, and $R^7$ is the phenyl or phenoxy group;

(ii) phosphites definable by the previous general formula, wherein $R^5$ and $R^6$ represent, jointly, a phenylene group, and $R^7$ is a phenoxy group;

(iii) an aromatic diphosphite to be represented by the formula:

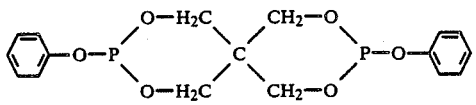

by interacting, per each mol of (a) compound, from 1 to 1.5 mol of (b) compound, from 0 to 1 mol of (c) compound, and from 0.5 to 1 mol of (d) compound.

A class of stabilizer siliconic compounds according to the present invention can be represented by the general formula:

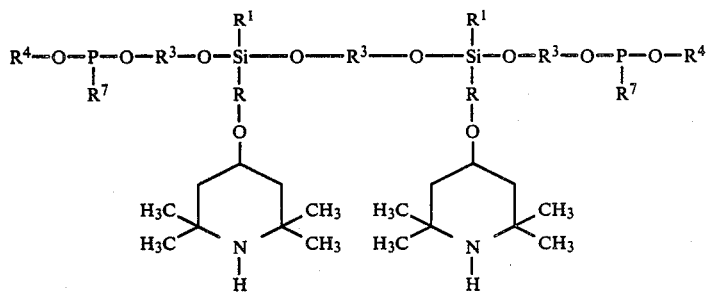

wherein R, $R^1$, $R^3$, $R^4$ and $R^7$ have the above indicated meaning.

These siliconic compounds can be generally obtained by reacting (a), (b), (c) and (d) with one another, in a mutual molar ratio equal to about 1:1:1:0.5, with the reactant (d) being either an aromatic phosphite or an aromatic phosphonite of (i) class.

Another class of stabilizer siliconic compounds according to the present invention can be represented by the general formula:

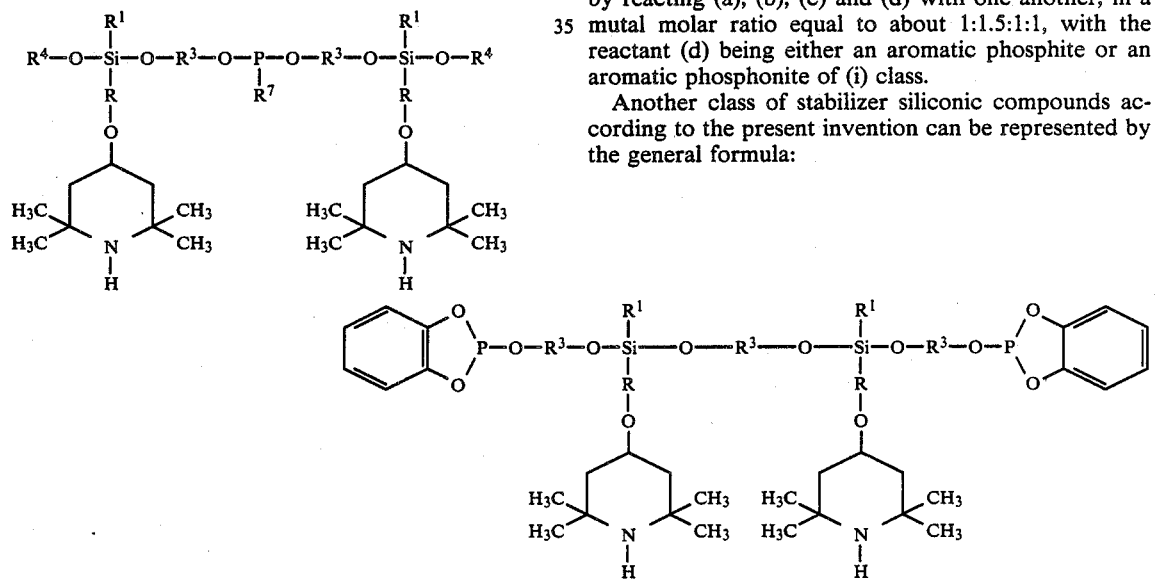

wherein R, $R^1$, $R^3$, $R^4$ and $R^7$ have the above indicated meaning.

These siliconic compounds can be generally obtained by reacting (a), (b), (c) and (d) with one another, in a mutal molar ratio equal to about 1:1.5:1:1, with the reactant (d) being either an aromatic phosphite or an aromatic phosphonite of (i) class.

Another class of stabilizer siliconic compounds according to the present invention can be represented by the general formula:

wherein R, $R^1$, $R^3$ have the above indicated meaning.

These siliconic compounds can be generally obtained by reacting (a), (b) and (d) with one another, in a mutal molar ratio equal to about 1:1.5:1, with the reactant (d) being a phosphite of (ii) class.

A further class of stabilizer siliconic compounds according to the present invention can be represented by the general formula:

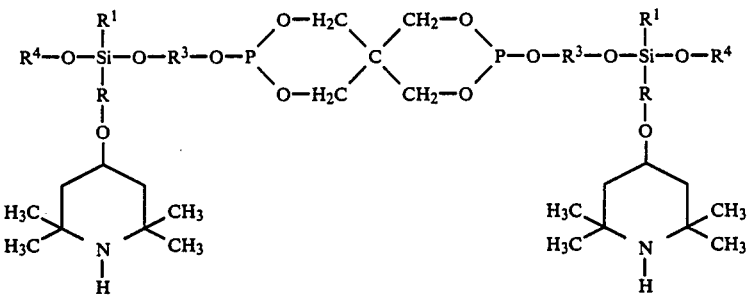

wherein R, $R^1$, $R^3$ and $R^4$ have the above indicated meaning.

These siliconic compounds can be generally obtained by reacting (a), (b), (c) and (d) with one another, in a mutal molar ratio equal to about 1:1:1:0.5, with the reactant (d) being a diphosphite of (iii) class.

The Process for the preparation of the stabilizer siliconic compounds according to the present invention comprises essentially the reaction of (a), (b), (c) and (d) under transesterification conditions, in the presence of transesterification catalysts.

However, in the preferred form of practical embodiment, (a), (b) and (c) are first reacted in the above indicated molar ratios, operating in the presence of a transesterification catalyst, under a nitrogen atmosphere, and continuously removing the methanol or ethanol which are formed as reaction byproducts. Catalysts suitable to the purpose are the alkali metal alkoxides, which are used in an amount of from 0.01 to 1% by weight in the reaction mixture. Temperatures suitable to the purpose may generally range from 80° to 120° C., and the related reaction times are of the order of 1–6 hours.

To the so-obtained reaction mixture, compound (d) is then added, in the already indicated molar proportions, and is reacted within the range of conditions as indicated for the first reaction step, but with a reduced pressure being maintained, for example of about 1 torr (133,32 Pa), with the phenol which forms as the reaction by product being continuously removed. This second reaction step requires generally times of the order of 1–2 hours.

At reaction complete, the obtained siliconic stabilizer compound is purified from the catalyst by neutralization with carbon dioxide gas, or with acetic acid. So, e.g., the recovery of the reaction product can be carried out by diluting the reaction mixture with a hydrocarbon solvent for facilitating the removal of the alkaline salts deriving from the transesterification catalyst, said salts being then separated by filtration or centifugation. The hydrocarbon solvent is then evaporated off, and the stabilizer siliconic compound is recovered as the residue from said evaporation.

The so-obtained siliconic stabilizer compounds show such structures as hereinabove defined, or they can be substantially represented by said structure, in as much as during their preparation process, a limited amount can be formed of more complex structures, which are still active as stabilizers for the organic polymers, and which hence need not be separated from the other reaction products.

In any case, the siliconic stabilizer compounds of the present invention have the physical form of more or less viscous oils, which can be directly added to the organic polymers to be stabilized.

Furthermore, said siliconic stabilizer compounds are perfectly compatible with the organic polymers, inside which they remain stably, and give to the same polymers higher stability characteristics than as obtainable when to the polymers equivalent amounts of sterically hindered amine and of aromatic phosphite are separately added.

By means of the siliconic stabilizer compounds of the present invention, the organic polymers in general can be stabilized, and in particular, the homopolymers and copolymers of the olefins and diolefins, such as polypropylene, polybutadiene and high- and low-density polyethylene, can be stabilized.

The stabilized polymeric compositions according to the present invention contain the organic polymer and an amount of at least one siliconic stabilizer compound, which supplies the composition with a nitrogen amount (deriving from the sterically hindered aminic function) comprised within the range of from 0.005 to 0.2% by weight and with a phosphorus amount (deriving from the aromatic phosphite or phosphonite function) of from 0.01 to 0.4% by weight.

The following experimental Examples are supplied to the purpose of illustrating the present invention without limiting it.

EXAMPLE 1

To a 100-ml flask, equipped with nitrogen inlet, Liebig condenser, flask for collecting the distillation products, and magnetic-bar stirrer, charged are: 2,2,6,6-tetramethyl-piperidinyl-4-oxypropyl-γ-methyl-dimethoxysilane (12.8 g; 40.26 mmol), n-butanol (3.68 ml; 40.26 mmol), hexanediol (4.75 g, 40.26 mmol) and sodium methoxide in the form of a 30% solution in methanol by weight (0.06 g; 0.3% by weight).

With a very slow flow of nitrogen being maintained through the flask, this latter is dipped in an oil bath kept at the controlled temperature of 105° C., and its contents are continuously stirred for 1 hour. During this time period, from the flask the methanol is removed, together with a small amount of butanol. At this point in time, to the flask triphenylphosphite (5.25 ml; 6.24 g; 20.13 mmol) is charged, and the reaction is continued for 30 minutes at the tenperature of 105° C., under the atmospheric pressure, and then for 40 minutes under reduced pressure (about 1 torr (133,32 Pa)). At the end of this time period, the phenol is completely collected inside the condenser, and the I.R. analysis of the product contained in the flask demonstrated the complete disappearance of the hydroxy groups.

The contents of the flask are diluted with 4 volumes of isooctane, and then to the flask small pieces of dry ice are added.

By so doing, a white solid (sodium carbonate) precipitates and is filtered off.

From the obtained filtrate the solvent is removed by vacuum flashing, and 19.07 g is obtained of a liquid and colourless product which, at the elemental analysis, shows the following composition: C=64.7% by weight; H=9.1% by weight; N=2.7% by weight; P=3.3% by weight.

This product, which shows to be highly stable at the thermogravimetric analysis, can be basically represented by the formula:

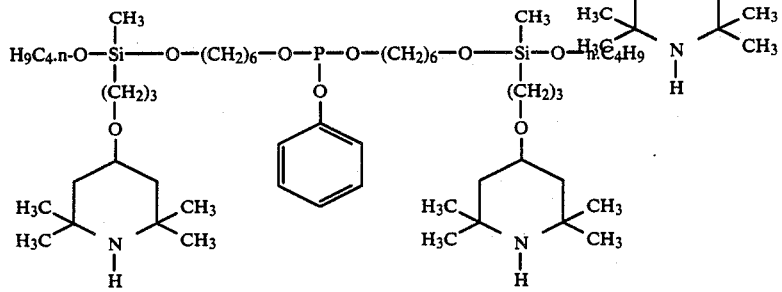

EXAMPLE 2

The process is carried out in the same way as disclosed in Example 1, by starting from 2,2,6,6-tetramethyl-piperidinyl-4-oxypropyl-γ-methyl-dimethoxysilane (4.08 g; 13.46 mmol), hexanediol (2.38 g; 20.18 mmol), n-butanol (1.23 ml; 0.998 g; 13.46 mmol); sodium methoxide (0.15 ml; 0.045 g) and diphenoxydiphenylphosphine (3.22 ml; 13.46 mmol). After the treatment of the reaction product as disclosed in Example 1, 9.8 g is obtained of a colourless liquid which, at the elemental analysis, shows the following composition: C=65.2% by weight; H=9.1% by weight; N=2.3% by weight; P=5.18% by weight.

This product can be substantially represented by the formula:

EXAMPLE 3

The process is carried out in the same way as disclosed in Example 1, by starting from 2,2,6,6-tetramethyl-piperidinyl-4-oxypropyl-γ-methyl-dimethoxysilane (4.38 g; 14.46 mmol), hexanediol (1.70 g; 14.46 mmol), n-butanol (1.32 ml; 1.07 g; 14.46 mmol); sodium methoxide (0.15 ml; 0.045 g) and diphenoxyphenylphosphine (2.12 ml; 7.22 mmol). After the treatment of the reaction product as disclosed in Example 1, 5.7 g is obtained of a colourless liquid which, at the elemental analysis, shows the following composition: C=65.2% by weight; H=9.4% by weight; N=2.4% by weight; P=3.7% by weight.

This product can be substantially represented by the formula:

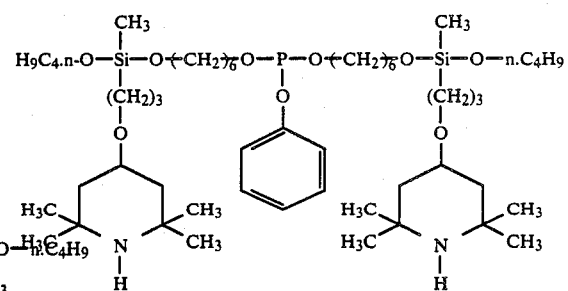

EXAMPLE 4

The process is carried out in the same way as disclosed in Example 1, by starting from 2,2,6,6-tetramethyl-piperidinyl-4-oxypropyl-γ-methyl-dimethoxysilane (4.1 g; 13.53 mmol), n-butanol (1.23 ml; 1.0 g: 13.53 mmol), hexanediol (1.46 g; 13.53 mmol), sodium methoxide (0.15 ml; 45 mg) and from a diphosphite, deriving from pentaerythritol, having the following formula:

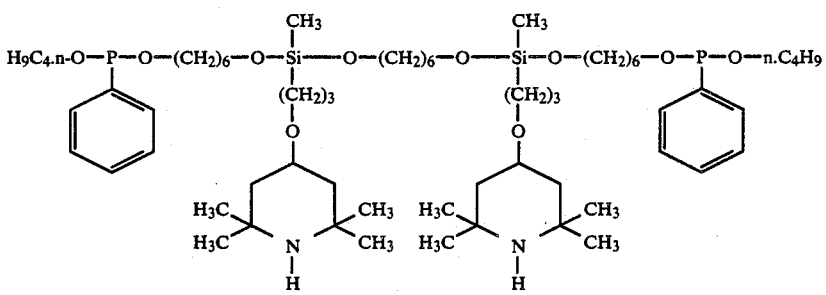

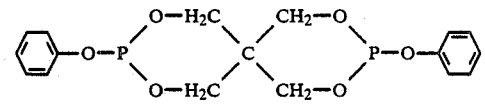

(1.70 g; 6.77 mmol). After the treatment of the reaction product as disclosed in Example 1, 5.1 g is obtained of a colourless liquid which, at the elemental analysis, shows the following composition: C=57.1% by weight; H=10.0% by weight; N=2.7% by weight; P=6.1% by weight.

This product can be substantially represented by the formula:

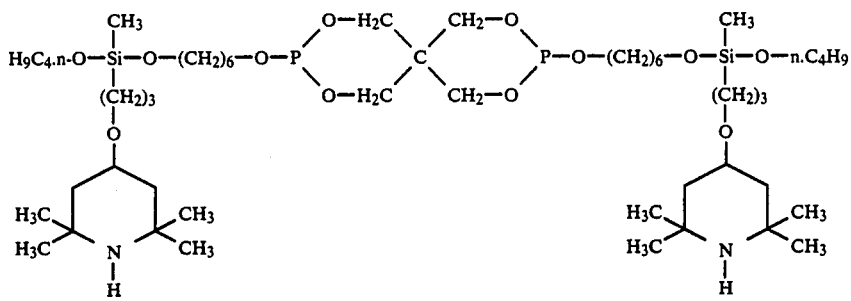

EXAMPLE 5

The process is carried out in the same way as disclosed in Example 1, by starting from 2,2,6,6-tetramethyl-piperidinyl-4-oxypropyl-γ-methyl-dimethoxysilane (4.25 g; 14.0 mmol), hexanediol (2.48 g; 21 mmol), sodium methoxide (0.15 ml; 45 mg) and benzophenyl phosphite (3.25 g; 14.0 mmol). The reaction product is diluted with diethyl ether and in then treated with 0.3 ml of acetic acid.

After separation and vacuum-drying, 7.5 g is obtained of a colourless liquid which, at the elemental analysis, shows a content of 2.4% by weight of N, and of 5.2% by weight of P.

This product can be substantially represented by the formula:

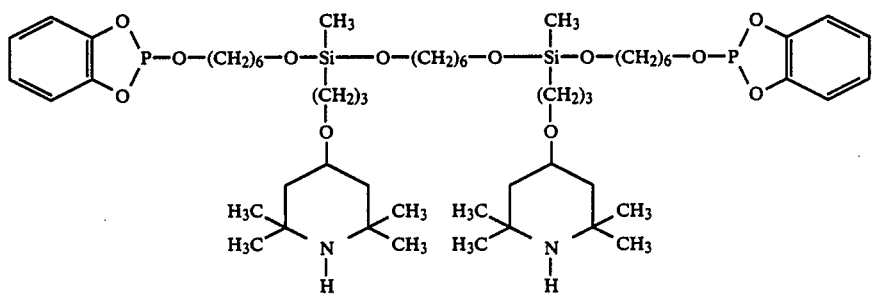

The siliconic stabilizer compounds prepared in the above examples are blended with polypropylene Moplefan ® FLF 20, by Montedison, and their capability is determined of inhibiting the polypropylene breakdown by means of accelerated ageing tests, both in laboratory (WOM and UV-Con), and outdoor, carried out on polypropylene film.

The stabilizing activity of the siliconic stabilizer compounds is compared to that of the commercial product TINUVIN 770, at the concentrations of 0.1, 0.25 and 0.5% by weight relatively to polypropylene. The amount of siliconic stabilizer compound present in polypropylene is in any case such as to secure an amount of nitrogen, deriving from the sterically hindered group, equalling the amount supplied by the commercial product TINUVIN 770, at the three above-shown concentrations.

Furthermore, to TINUVIN 770 the commercial product SANDOSTAB PEPQ is added in such an amount as to yield a phosphorus amount equal to that supplied by the siliconic stabilizer compounds according to the present invention.

Furthermore, all of the samples are formulated with a fixed amount of process stabilizer: BHT (2,5-ditert.butyl-4-methylphenol), and equal to 0.2% by weight relatively to polypropylene.

The blending of the composition components is carried out, in all cases, on a DIOSNA mixer, over a 30-minute time. The so-prepared powders are granulated in an extruder provided with a reps filter, and with a screw having a 1:4 compression ratio, at the revolution speed of 30 rpm and with the following temperature profile: 190°, 235°, 270°, 270° C.

The so obtained granule is then extruded again on the same extruder, equipped with an outfit for film production, with the following modalities: 60 rpm; temperature profile: 175°, 200°, 210°, 220° C. In such a way, a film is obtained, which has a thickness of about 50 μm, to be submitted to the ageing tests.

The ageing in UV-con is carried out by means of a device supplied by ATLAS, capable of submitting the polymeric films to alternate cycles of lighting with a UV fluorescence lamp and of condensation in the dark. The lighting step has a duration of 8 hours at the temperature of the black panel of 60° C., and the condensation step has a duration of 4 hours at 40° C.

For the ageing in Weather-O-Meter (WOM), the instrument ATLAS GJ65 is used, programmed with a full-light cycle at the temperature of the black panel of 60° C., and at a relative humidity of 90%.

The outdoor ageing is carried out in the region of Asiago (Italy), at a height of about 1,000 meters above sea level, for a time of 8 months (April through November).

For evaluating the degradation level reached by the polymeric composition, in all of the ageing tests, the value of elongation at break according to ASTM-D882 Standard is assumed (Tables 1, 3, 5, 7, 9 and 10). The degradation performed under UV-Con and on WOM is furthermore continued until the sample crumbles, with the comparison bein performed with the behaviour of the corresponding polymeric films for the various additive compositions (Tables 2, 4, 6 and 8).

TABLE 1

Exposure Time as Hours in WOM Necessary for Reducing by 50% the Initial Value of Elongation at Break of the Polypropylene Film

| Stabilizer | Sample A | Sample B | Sample C |
|---|---|---|---|
| None | 30 hours | — | — |
| Example 1 | 370 hours | 660 hours | 850 hours |
| TINUVIN 770 | 255 hours | 320 hours | 525 hours |

NOTE:
Sample A 0.1% by weight of TINUVIN 770, or an equivalent amount of the siliconic stabilizer compound of Example 1; 0.2% by weight of BHT.
Sample B 0.25% by weight of TINUVIN 770, or an equivalent amount of the siliconic stabilizer compound of Example 1, 0.2% by weight of BHT.
Sample C 0.5% by weight of TINUVIN 770, or an equivalent amount of the siliconic stabilizer compound of Example 1; 0.2% by weight of BHT.

In the compositions with TINUVIN 770, an amount was furthermore added of the commercial phosphite SANDOSTAB PEPQ, equivalent to the phosphorus content in the siliconic stabilizer compound of Example 1.

TABLE 2

Exposure Time as Hours in WOM Necessary for Crumbling a Sample of the Polymeric Film

| Stabilizer | Sample A | Sample B | Sample C |
|---|---|---|---|
| None | 50 hours | — | — |
| Example 1 | 420 hours | 860 hours | >1000 hours |
| TINUVIN 770 | 370 hours | 525 hours | 865 hours |

NOTE:
Sample A 0.1% by weight of TINUVIN 770, or an equivalent amount of the siliconic stabilizer compound of Example 1; 0.2% by weight of BHT.
Sample B 0.25% by weight of TINUVIN 770, or an equivalent amount of the siliconic stabilizer compound of Example 1, 0.2% by weight of BHT.
Sample C 0.5% by weight of TINUVIN 770, or an equivalent amount of the siliconic stabilizer compound of Example 1; 0.2% by weight of BHT.

In the compositions with TINUVIN 770, an amount was furthermore added of the commercial phosphite SANDOSTAB PEPQ, equivalent to the phosphorus content in the siliconic stabilizer compound of Example 1.

TABLE 3

Exposure Time as Hours in WOM Necessary for Reducing by 50% the Initial Value of Elongation at Break of the Polymeric Film

| Stabilizer | Sample A | Sample B | Sample C |
|---|---|---|---|
| None | 30 hours | — | — |
| Example 2 | 295 hours | 465 hours | 640 hours |
| Example 4 | 310 hours | 580 hours | 860 hours |
| TINUVIN 770 | 180 hours | 245 hours | 355 hours |

NOTE:
Sample A 0.1% by weight of TINUVIN 770, or an equivalent amount of the siliconic stabilizer compound of Example 2 or 4; 0.2% by weight of BHT.
Sample B 0.25% by weight of TINUVIN 770, or an equivalent amount of the siliconic stabilizer compound of Example 2 or 4, 0.2% by weight of BHT.
Sample C 0.5% by weight of TINUVIN 770, or an equivalent amount of the siliconic stabilizer compound of Example 2 or 4; 0.2% by weight of BHT.

In the compositions with TINUVIN 770, an amount was furthermore added of the commercial phosphite SANDOSTAB PEPQ, equivalent to the phosphorus content in the siliconic stabilizer compound of Example 2 or 4.

TABLE 4

Exposure Time as Hours in WOM Necessary for Crumbling a Sample of the Polymeric Film

| Stabilizer | Sample A | Sample B | Sample C |
|---|---|---|---|
| None | 5 hours | — | — |
| Example 2 | 470 hours | 610 hours | 843 hours |
| Example 4 | 510 hours | 790 hours | >1000 hours |
| TINUVIN 770 | 215 hours | 320 hours | 475 hours |

NOTE:
Sample A 0.1% by weight of TINUVIN 770, or an equivalent amount of the siliconic stabilizer compound of Example 2 or 4; 0.2% by weight of BHT.
Sample B 0.25% by weight of TINUVIN 770, or an equivalent amount of the siliconic stabilizer compound of Example 2 or 4, 0.2% by weight of BHT.
Sample C 0.5% by weight of TINUVIN 770, or an equivalent amount of the siliconic stabilizer compound of Example 2 or 4; 0.2% by weight of BHT.

In the compositions with TINUVIN 770, an amount was furthermore added of the commercial phosphite SANDOSTAB PEPQ, equivalent to the phosphorus content in the siliconic stabilizer compound of Example 2 or 4.

TABLE 5

Exposure Time as Hours in UV-Con Necessary for Reducing by 50% the Initial Value of Elongation at Break of the Polymeric Film

| Stabilizer | Sample A | Sample B | Sample C |
|---|---|---|---|
| None | 20 hours | — | — |
| Example 1 | 265 hours | 315 hours | 400 hours |
| TINUVIN 770 | 205 hours | 260 hours | 345 hours |

NOTE:
Sample A 0.1% by weight of TINUVIN 770, or an equivalent amount of the siliconic stabilizer compound of Example 1; 0.2% by weight of BHT.
Sample B 0.25% by weight of TINUVIN 770, or an equivalent amount of the siliconic stabilizer compound of Example 1; 0.2% by weight of BHT.
Sample C 0.5% by weight of TINUVIN 770, or an equivalent amount of the siliconic stabilizer compound of Example 1; 0.2% by weight of BHT.

In the compositions with TINUVIN 770, an amount was furthermore added of the commercial phosphite SANDOSTAB PEPQ, equivalent to the phosphorus content in the siliconic stabilizer compound of Example 1.

TABLE 6

Exposure Time as Hours in UV-Con Necessary for Crumbling a Sample of the Polymeric Film

| Stabilizer | Sample A | Sample B | Sample C |
|---|---|---|---|
| None | 30 hours | — | — |
| Example 1 | 315 hours | 416 hours | 520 hours |
| TINUVIN 770 | 265 hours | 325 hours | 460 hours |

NOTE:
Sample A 0.1% by weight of TINUVIN 770, or an equivalent amount of the siliconic stabilizer compound of Example 1; 0.2% by weight of BHT.
Sample B 0.25% by weight of TINUVIN 770, or an equivalent amount of the siliconic stabilizer compound of Example 1, 0.2% by weight of BHT.
Sample C 0.5% by weight of TINUVIN 770, or an equivalent amount of the siliconic stabilizer compound of Example 1; 0.2% by weight of BHT.

In the compositions with TINUVIN 770, an amount was furthermore added of the commercial phosphite SANDOSTAB PEPQ, equivalent to the phosphorus content in the siliconic stabilizer compound of Example 1.

TABLE 7

Exposure Time as Hours in UV-Con Necessary for Reducing by 50% the Initial Value of Elongation at Break of the Polymeric Film

| Stabilizer | Sample A | Sample B | Sample C |
|---|---|---|---|
| None | 20 hours | — | — |
| Example 2 | 240 hours | 330 hours | 400 hours |
| Example 4 | 275 hours | 380 hours | 410 hours |

TABLE 7-continued

Exposure Time as Hours in UV-Con Necessary for Reducing by 50% the Initial Value of Elongation at Break of the Polymeric Film

| Stabilizer | Sample A | Sample B | Sample C |
|---|---|---|---|
| TINUVIN 770 | 128 hours | 175 hours | 210 hours |

NOTE:
Sample A 0.1% by weight of TINUVIN 770, or an equivalent amount of the siliconic stabilizer compound of Example 2 or 4; 0.2% by weight of BHT.
Sample B 0.25% by weight of TINUVIN 770, or an equivalent amount of the siliconic stabilizer compound of Example 2 or 4; 0.2% by weight of BHT.
Sample C 0.5% by weight of TINUVIN 770, or an equivalent amount of the siliconic stabilizer compound of Example 2 or 4; 0.2% by weight of BHT.

In the compositions with TINUVIN 770, an amount was furthermore added of the commercial phosphite SANDOSTAB PEPQ, equivalent to the phosphorus content in the siliconic stabilizer compound of Example 2 or 4.

TABLE 8

Exposure Time as Hours in UV-Con Necessary for Crumbling a Sample of the Polymeric Film

| Stabilizer | Sample A | Sample B | Sample C |
|---|---|---|---|
| None | 30 hours | — | — |
| Example 2 | 285 hours | 373 hours | 494 hours |
| Example 4 | 350 hours | 465 hours | 530 hours |
| TINUVIN 770 | 173 hours | 210 hours | 245 hours |

NOTE:
Sample A 0.1% by weight of TINUVIN 770, or an equivalent amount of the siliconic stabilizer compound of Example 2 or 4; 0.2% by weight of BHT.
Sample B 0.25% by weight of TINUVIN 770, or an equivalent amount of the siliconic stabilizer compound of Example 2 or 4, 0.2% by weight of BHT.
Sample C 0.5% by weight of TINUVIN 770, or an equivalent amount of the siliconic stabilizer compound of Example 2 or 4; 0.2% by weight of BHT.

In the compositions with TINUVIN 770, an amount was furthermore added of the commercial phosphite SANDOSTAB PEPQ, equivalent to the phosphorus content in the siliconic stabilizer compound of Example 2 or 4.

TABLE 9

Percent residual Value of Elongation at Break, Relatively to the Initial Value of Polymeric Films Kept Standing Outdoor

| Stabilizer | Sample A | | Sample B | | Sample C | |
|---|---|---|---|---|---|---|
| | April July | August November | April July | August November | April July | August November |
| None | broken | — | — | — | — | — |
| Example 1 | 100 | 71.5 | 100 | 72.3 | 100 | 75.1 |
| TINUVIN 770 | 100 | 70.0 | 100 | 72.3 | 100 | 72.7 |

NOTE:
Sample A 0.1% by weight of TINUVIN 770, or an equivalent amount of the siliconic stabilizer compound of Example 1; 0.2% by weight of BHT.
Sample B 0.25% by weight of TINUVIN 770, or an equivalent amount of the siliconic stabilizer compound of Example 1, 0.2% by weight of BHT.
Sample C 0.5% by weight of TINUVIN 770, or an equivalent amount of the siliconic stabilizer compound of Example 1; 0.2% by weight of BHT.

In the compositions with TINUVIN 770, an amount was furthermore added of the commercial phosphite SANDOSTAB PEPQ, equivalent to the phosphorus content in the siliconic stabilizer compound of Example 1.

TABLE 10

Percent Residual Value of Elongation at Break, Relatively to the Initial Value of Polymeric Films Kept Standing Outdoor

| Stabilizer | Sample A | | Sample B | | Sample C | |
|---|---|---|---|---|---|---|
| | April July | August November | April July | August November | April July | August November |
| None | broken | — | — | — | — | — |
| Example 2 | 100 | 64.6 | 100 | 67.1 | 100 | 67.3 |
| Example 4 | 100 | 65.1 | 100 | 68.2 | 95 | 70.5 |
| Example 6 | 100 | 60.2 | 100 | 52.1 | 78 | 43.0 |
| TINUVIN 770 | 100 | broken | 100 | broken | 100 | broken |

NOTE:
Sample A 0.1% by weight of TINUVIN 770, or an equivalent amount of the siliconic stabilizer compound of Example 2, 4 or 6; 0.2% by weight of BHT.
Sample B 0.25% by weight of TINUVIN 770, or an equivalent amount of the siliconic stabilizer compound of Example 2, 4 or 6, 0.2% by weight of BHT.
Sample C 0.5% by weight of TINUVIN 770, or an equivalent amount of the siliconic stabilizer compound of Example 2, 4 or 6; 0.2% by weight of BHT.

In the compositions with TINUVIN 770, an amount was furthermore added of the commercial phosphite SANDOSTAB PEPQ, equivalent to the phosphorus content in the siliconic stabilizer compound of Example 2, 4 or 6.

We claim:

1. Siliconic stabilizer compounds for organic polymers, comprising the general formula:

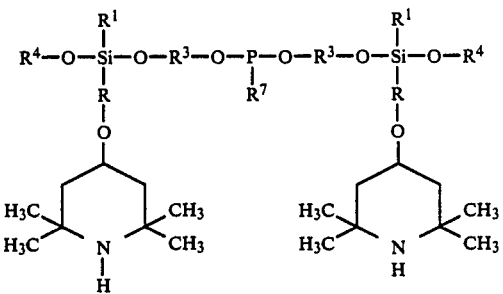

wherein R is a linear or branched alkylene group containing from 1 to 6 carbon atoms; $R^1$ and $R^2$ are, independently, a methyl or ethyl group; $R^3$ is a linear or branched alkylene group containing from 4 to 12 carbon atoms, or a cycloalkylene group; $R^4$ is a linear or branched alkyl group containing from 1 to 10 carbon atoms; $R^5$ and $R^6$ are, jointly, phenyl groups or phenylene groups; and $R^7$ is a phenyl or phenoxy group when $R^5$ and $R^6$ are phenyl groups, and $R^7$ is a phenoxy group when $R^5$ and $R^6$ are phenylene groups.

2. Compounds according to claim 1, wherein R is an alkylene group containing 3 carbon atoms; $R^3$ is an alkylene group containing 6 carbon atoms; and $R^4$ is an alkyl group containing 4 carbon atoms.

3. Siliconic stabilizer compounds for organic polymers, comprising the general formula:

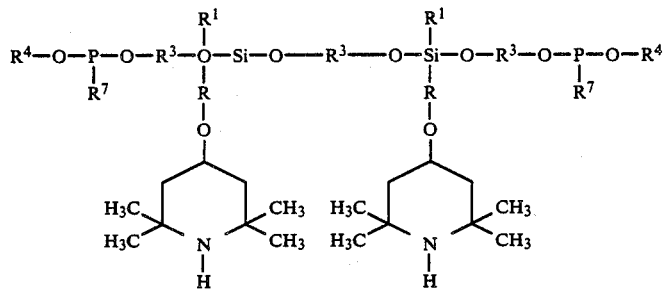

wherein R is a linear or branched alkylene group containing from 1 to 6 carbon atoms; $R^1$ is a methyl or ethyl group; $R^3$ is a linear or branched alkylene group containing from 4 to 12 carbon atoms, or a cycloalkylene group; $R^4$ is a linear or branched alkyl group containing from 1 to 10 carbon atoms; and $R^7$ is a phenoxy group.

4. Compounds according to claim 3, wherein R is an alkylene group with 3 carbon atoms; $R^3$ is an alkylene group containing 6 carbon atoms; and $R^4$ is an alkyl group containing 4 carbon atoms.

5. Siliconic stabilizer compounds for organic polymers, comprising the general formula:

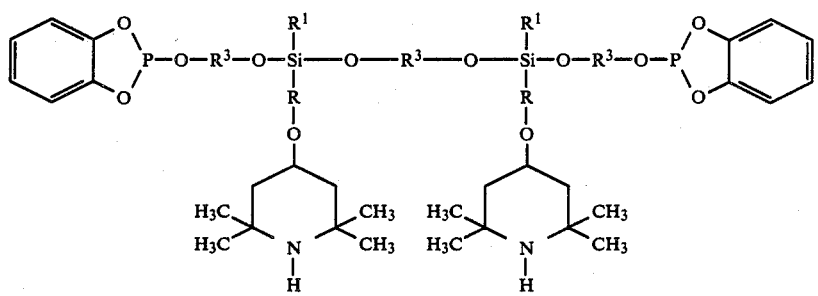

wherein R is a linear or branched alkylene group containing from 1 to 6 carbon atoms; $R^1$ is a methyl or ethyl group; and $R^3$ is a linear or branched alkylene group containing from 4 to 12 carbon atoms, or a cycloalkylene group.

6. Compounds according to claim 5, wherein R is an alkylene group containing 3 carbon atoms; $R_3$ is an alkylene group containing 6 carbon atoms; and $R^4$ is an alkyl group containing 4 carbon atoms.

7. Siliconic stabilizer compounds for organic polymers, comprising the general formula:

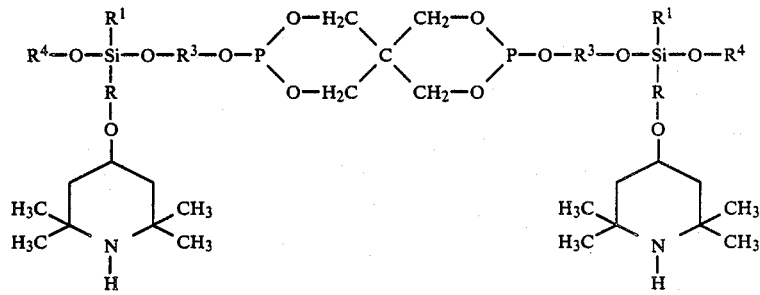

wherein R is a linear or branched alkylene group containing from 1 to 6 carbon atoms; $R^1$ is a methyl or ethyl group; $R^3$ is a linear or branched alkylene group containing from 4 to 12 carbon atoms, or a cycloalkylene group; and $R^4$ is a linear or branched alkyl group containing from 1 to 10 carbon atoms.

8. Compounds according to claim 7, wherein R is an alkylene group containing 3 carbon atoms; $R^3$ is an alkylene group containing 6 carbon atoms; and $R^4$ is an alkyl group containing 4 carbon atoms.

9. Stabilized compositions of organic polymers, comprising an organic polymer and a stabilizer amount of at least one of the siliconic stabilizer compounds according to claims 1, 3, 5 and 7.

10. Compositions according to claim 9, wherein said organic polymer is an olefinic or diolefinic homopolymer or copolymer.

* * * * *

UNITED STATES PATENT AND TRADEMARK OFFICE
CERTIFICATE OF CORRECTION

PATENT NO. :   4,778,838

DATED      :   October 18, 1988

INVENTOR(S) :  Alberto Greco
               Carlo Busetto

It is certified that error appears in the above-identified patent and that said Letters Patent is hereby corrected as shown below:

On columns 7 and 8, the formula on column 7, line 12 has been superimposed on the formula on column 8, line 5.  Please rewrite the formulae as follows:

On column 7, line 12, the correct formula is

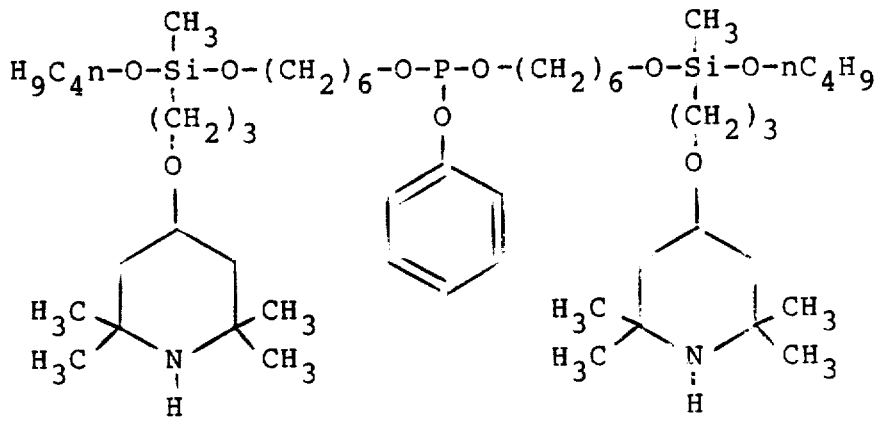

UNITED STATES PATENT AND TRADEMARK OFFICE
CERTIFICATE OF CORRECTION

PATENT NO. : 4,778,838

DATED : October 18, 1988

INVENTOR(S) : Alberto Greco
Carlo Busetto

It is certified that error appears in the above-identified patent and that said Letters Patent is hereby corrected as shown below:

On Column 8, line 5, the correct formula is:

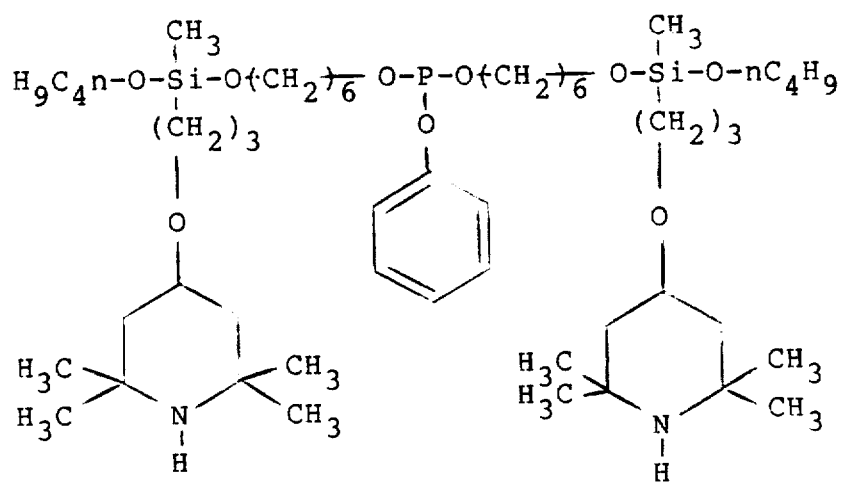

UNITED STATES PATENT AND TRADEMARK OFFICE
CERTIFICATE OF CORRECTION

PATENT NO. : 4,778,838

DATED : October 18, 1988

INVENTOR(S) : Alberto Greco
Carlo Busetto

It is certified that error appears in the above-identified patent and that said Letters Patent is hereby corrected as shown below:

On Column 15, line 1 rewrite the formula to read

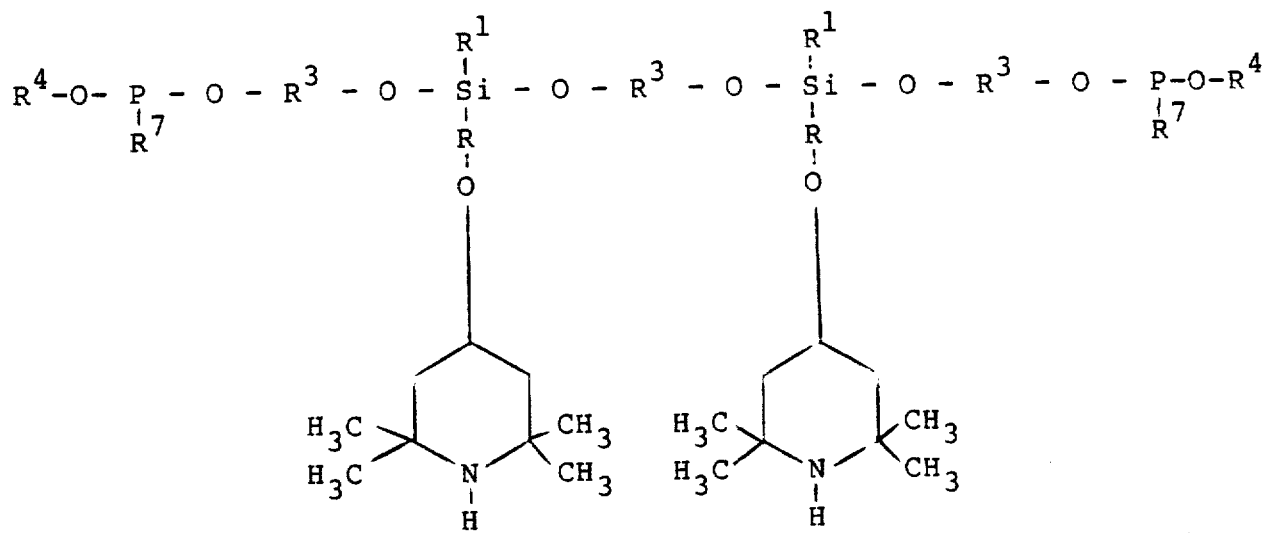

Signed and Sealed this

Fifteenth Day of October, 1991

*Attest:*

HARRY F. MANBECK, JR.

*Attesting Officer*  *Commissioner of Patents and Trademarks*